(12) United States Patent
Panin

(10) Patent No.: US 6,280,752 B1
(45) Date of Patent: Aug. 28, 2001

(54) VITAMIN E ACETATE-BASED HYDROPHOBIC GEL FORMULATION FOR TOPICAL APPLICATION

(75) Inventor: Giorgio Panin, Via Vittorio Veneto 48/b, I-45100 Rovigo (IT)

(73) Assignee: Giorgio Panin, Rovigo (IT)

( * ) Notice: Subject to any disclaimer, the term of this patent is extended or adjusted under 35 U.S.C. 154(b) by 0 days.

(21) Appl. No.: 09/405,224

(22) Filed: Sep. 27, 1999

(30) Foreign Application Priority Data

Sep. 25, 1998 (IT) .............................................. MI98A2075

(51) Int. Cl.⁷ ........................ A61K 31/355; A61K 47/02; A61K 47/06; A61K 47/22; A61K 47/44
(52) U.S. Cl. .................. 424/401; 424/78.02; 424/78.03; 424/78.06; 424/731; 424/489; 514/844; 514/944; 549/408; 106/287.13; 554/219
(58) Field of Search ................................ 424/401, 78.02, 424/489, 78.06, 78.03, 731; 514/844, 944; 554/219; 549/408; 106/287.13

(56) References Cited

U.S. PATENT DOCUMENTS 4,410,517 * 10/1983 Stillman et al. ...................... 424/195
4,551,332 * 11/1985 Stillman et al. .................. 424/195.1
6,013,270 * 8/1998 Hargraves et al. .................. 424/401
6,146,664 * 7/1998 Siddiqui et al. ..................... 424/489

FOREIGN PATENT DOCUMENTS

WO 98 10793    3/1998  (WO).

\* cited by examiner

*Primary Examiner*—Diana Dudash
*Assistant Examiner*—Mina Haghighatian
(74) *Attorney, Agent, or Firm*—Sughrue, Mion, Zinn, Macpeak & Seas, PLLC

(57) ABSTRACT

A formulation for topical use in hydrophobic gel form comprising, in weight percentages on the total weight of the formulation:

20 to 70% of vitamin E acetate,
  20 to 70% of a volatile silicone chosen from the group comprising pentamer cyclomethicone tetramer cyclomethicone, hexamer cyclomethicone, hexamethyldisiloxane and mixtures thereof
  to 13% of hydrogenated castor oil.

10 Claims, No Drawings

VITAMIN E ACETATE-BASED HYDROPHOBIC GEL FORMULATION FOR TOPICAL APPLICATION

TECHNICAL FIELD

The present invention relates in general to a formulation for topical use and, in particular, to a vitamin E acetate-based hydrophobic gel preparation.

BACKGROUND OF THE INVENTION

Vitamin E and its derivatives are substances which by virtue of their presumed properties as antioxidants and removers of free radicals, are widely used in the pharmaceutics and cosmetics industry in the preparation of formulations for treating skin diseases, or for combating or preventing unsightly skin conditions.

For these reasons, vitamin E and its derivatives are often present in cosmetic formulations as "active" components in variable concentrations ranging between 1% and 25%, although the antioxidant and anti-ageing action of vitamin E at a skin level has never been scientifically proved.

On the contrary, it has recently been experimentally proved (see patent application WO 98/10793 by the same Applicant) that vitamin E acetate has physical-chemical properties such as to make it suitable for use as main component of the lipophilic phase of ointments.

In fact, vitamin E acetate is particularly easy to spread, is absorbed surprisingly quickly, produces no unpleasant thermal sensations, leaves the skin shiny only for a few minutes, and then leaves it soft, elastic and not sticky; in addition, it resists to cleansing with water or detergents.

In addition, since vitamin E acetate is not a molecule foreign to the human organism, it can easily integrate with the lipids present in the cornified layer, thus facilitating absorption through the skin of substances dispersed into it.

Among the other formulations for topical use, the above patent application disclosed and claimed a hydrophobic gel preparation comprising a cyclomethicone and dimethiconol mixture, preferably having a 8:2 weight ratio.

Two examples of said formulation had been provided, too, in which vitamin E acetate made up 20% and 30% respectively of the total weight of the composition, the rest of which comprised a 8:2 cyclomethicone/dimethiconol mixture and, optionally, 5% of hydrogenated castor oil.

These hydrophobic gels actually proved excellent formulations for cosmetic use when used as they are, and very good carriers of pharmaceutically active substances.

Nevertheless, it has been observed that hydrophobic gels thus formulated in the end showed a certain tendency to separate a liquid phase, i.e. a certain tendency to syneresis.

SUMMARY OF THE INVENTION

The problem underlying the present invention was that of providing a vitamin E acetate-based hydrophobic gel that could overcome the inconveniences shown by the hydrophobic gels that were already known from previous patent application WO 98/10793, while at the same time keeping unchanged the excellent properties as cosmetics and as carriers for active principles of the latter.

According to the invention, such a problem has been solved by a hydrophobic gel formulation for topical use comprising, in weight percentages on the total weight of the formulation, 20 to 70% of vitamin E acetate, 20 to 70% of a volatile silicone chosen from the group comprising pentamer cyclomethicone (or decamethylcyclopentasiloxane), tetramer cyclomethicone (or octamethylcyclotetrasiloxane), hexamer cyclomethicone and mixtures thereof, hexamethyldisiloxane, and 7 to 13% of hydrogenated castor oil.

The content of vitamin E acetate is preferably comprised between 30 and 60%.

Preferably, the formulation according to the invention also comprises 7 to 15% of an oily component chosen among vegetal oils and esters of fatty acids such as octyl palmitate, isopropyl myristate and ethyl oleate or mixtures thereof, for the purpose of further incrementing the gel stability and ensuring that no phase separation at all occurs in time.

In addition, the formulation can also comprise 2 to 3% of dimethiconol for the purpose of increasing the tactile sensation of silkiness of the skin that is felt during and after the application of the gel.

The hydrophobic gel according to the invention is characterised by absolute stability over the time and towards high and low temperatures in terms of viscosity and of rheological features and it does not show the slightest phenomenon of syneresis not even several months after the preparation.

The gel according to the invention can be very easily spread over the skin, and it is of absolutely pleasant application since it does not produce any thermal sensation on the skin and is absorbed with great rapidity.

The application of the gel according to the invention causes the formation of a thin film on the skin, which is absolutely invisible since it is not shiny. This film protects the skin for a long time against any aggression by external, atmospheric, physical and chemical agents avoiding the removal of the hydrolipidic film naturally occurring on the skin. In fact, it integrates the above film by bringing in a significant amount of vitamin E acetate.

After application of the hydrophobic gel according to the invention, the skin is extremely soft and silky.

The hydrophobic gel according to the invention is remarkably suitable to be used as a base ointment in which pharmaceutically active substances can be dissolved or suspended, also thanks to its easy applicability and to its rapid absorption by the skin.

Some examples of active principles that can be carried in the hydrophobic gel according to the invention comprise antibiotics, such as gentamicin, neomycin, clindamycin, and tetracyclines, corticosteroids, such as hydrocortisone acetate or butyrate, diflucortolone valerate, methylprednisolone aceponate, mometasone furoate and the esters of betametasone, trans-retinoic acid, synthetic retinoids, calcipotriol, vitamins such as retinol and its derivatives (retinol acetate and palmitate), lipophilic derivatives of ascorbic acid, such as palmitoylascorbic acid, vitamin K, vitamin D, vasoprotectants such as flavonoids and topical anti-inflammatory agents.

DETAILED DESCRIPTION OF THE INVENTION

For the purpose of further illustrating the present invention, the following general example shows a way to prepare a hydrophobic gel according to the invention.

EXAMPLE

| Pentamer cyclomethicone 245 | 39.5% |
|---|---|
| Vitamin E acetate | 30.0% |
| Hydrogenated castor oil | 10.5% |
| Octyl palmitate | 10.0% |
| 8:2 Cyclomethicone/dimethiconol | 10.0% |

525 g of hydrogenated castor oil (Cutina HR) and 500 g of octyl palmitate were introduced into a steel-turbine mixer (manufactured by Dumec), and the content was stirred while being heated at about 80–90° temperature until the hydrogenated castor oil dissolved.

Then, 1500 g of vitamin E acetate were added under stirring at the above temperature, and the vacuum was produced inside the mixer (vacuum equal to 600 cmHg).

Once the desired degree of vacuum had been achieved, 500 g of a preformed mixture of 8:2 pentamer cyclomethicone/dimethiconol and 1975 g of pentamer cyclomethicone 245 were added under stirring.

The homogeneous mixture thus obtained was brought to ambient temperature under continuous stirring so as to obtain, in the end, a translucent hydrophobic gel of semisolid consistence.

100 small plastic jars containing 50 g each were filled with the gel prepared in this way and said jars were properly closed and subjected to a conservation test at different temperatures: –20° C., 3° C. and 30° C. for 90 days, and 60° C. for 21 days.

The aspect of the cream remained unchanged during the entire period of conservation at the above four temperatures, as well as its viscosity and the other rheological characteristics.

Significantly, no phenomenon of phase separation nor collapse of the three-dimensional structure of the gel was noted not even at the end of the test at 60° C.

The moisturising effect of the hydrophobic gel according to the invention was assessed by skin comeometry with the aid of an instrument called Corneometer, that is to say, a special capacitance meter which, through a cutaneous probe, allows measuring the variations in the skin capacitance caused by a higher or lower content of water in the most superficial layers of the epidermis.

For the purpose of making the above evaluation, 10 female subjects were asked to apply the gel prepared according to the above example on the back of their left hand and on the medial surface of their left forearm every 12 hours with slight massage. They were also asked to apply in the same way vaseline oil on the back of their right hand and on the medial surface of their right forearm.

The subjects were examined for a three-day period, during which they frequently washed their hands with detergents or soaps, whereas their forearm was washed only every 24 hours.

Each day, a basal measurement ($T_0$) was made followed by measurements 3 minutes, 5 hours and 10 hours after application.

The average of the measurements gave the results summarized in the following table:

| HYDROPHOBIC GEL | | | | VASELINE OIL | | | |
|---|---|---|---|---|---|---|---|
| Left | hand | Left | Forearm | Right | hand | Right | Forearm |
| $T_0$ | 56 | $T_0$ | 55 | $T_0$ | 57 | $T_0$ | 55 |
| 3 m | 50 | 3 m | 46 | 3 m | 47 | 3 m | 53 |
| 5 h | 61 | 5 h | 59 | 5 h | 58 | 5 h | 56 |
| 10 h | 63 | 10 h | 62 | 10 h | 57 | 10 h | 56 |

From the analysis of the values reported in the table, it can be deduced that the hydrophobic gel according to the invention brought about a significant increase of the skin moisturization, whereas the vaseline oil did not modify it substantially.

I claim:

1. A formulation for topical use in hydrophobic gel form comprising, in weight percentages on the total weight of the formulation:

20 to 70% of vitamin E acetate, 20 to 70% of a volatile silicone chosen from the group consisting of pentamer cyclomethicone, tetramer cyclomethicone, hexamer cyclomethicone, hexamethyldisiloxane and mixtures thereof, 7 to 13% of hydrogenated castor oil.

2. A formulation for topical use according to claim 1, which comprises 30 to 60% of vitamin E acetate.

3. A formulation for topical use according to claim 2, wherein said volatile silicone is pentamer cyclomethicone.

4. A formulation for topical use according to claim 3, further comprising 7 to 15% of an oily component chosen amount vegetable oils and esters of fatty acids.

5. A formulation for topical use according to claim 4, further comprising 2 to 3% of dimethiconol.

6. A formulation for topical use according to claim 5, having the following composition:

| Pentamer cyclomethicone | 47.5% |
|---|---|
| Vitamin E acetate | 30.0% |
| Hydrogenated castor oil | 10.5% |
| octyl palmitate | 10.0% |
| Dimethiconol | 2.0%. |

7. An excipient for pharmaceutically active substances to be topically applied comprising a formulation according to claim 1.

8. An excipient for pharmaceutically active substances to be topically applied comprising a formulation according to claim 4.

9. A pharmaceutical composition for topical application comprising a formulation according to claim 1 and at least one pharmaceutically active substance.

10. A pharmaceutical composition for topical application comprising a formulation according to claim 4 and at least one pharmaceutically active substance.

* * * * *